United States Patent
Taylor et al.

(10) Patent No.: US 6,706,135 B2
(45) Date of Patent: Mar. 16, 2004

(54) PROCESS FOR TEMPORARILY STABILIZING AN EXTENSIBLE WEB

(75) Inventors: Jack Draper Taylor, Roswell, GA (US); Stephen Clark Smith, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 241 days.

(21) Appl. No.: 10/036,842

(22) Filed: Dec. 21, 2001

(65) Prior Publication Data
US 2003/0116271 A1 Jun. 26, 2003

(51) Int. Cl.[7] .................. A61F 13/15; D04H 3/08; D06C 25/00
(52) U.S. Cl. .............. 156/267; 156/73.1; 156/184; 156/269; 156/271; 156/290; 156/291; 156/308.4
(58) Field of Search .............. 156/73.1, 184, 156/267, 269–271, 290–291, 308.4

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,560,292 A | 2/1971 | Butter |
| 3,641,638 A | 2/1972 | Laible |
| 3,692,618 A | 9/1972 | Dorschner et al. |
| 3,802,817 A | 4/1974 | Matsuki et al. |
| 3,849,241 A | 11/1974 | Butin et al. |
| 4,100,324 A | 7/1978 | Anderson et al. |
| 4,340,563 A | 7/1982 | Appel et al. |
| 4,610,685 A | 9/1986 | Raley |
| 4,720,415 A | 1/1988 | Vander Wielen et al. |
| 4,854,984 A | 8/1989 | Ball et al. |
| 4,919,738 A | 4/1990 | Ball et al. |
| 5,114,781 A | 5/1992 | Morman |
| 5,116,662 A | 5/1992 | Morman |
| 5,171,388 A | 12/1992 | Hoffman et al. |
| 5,766,411 A | 6/1998 | Wilson |
| 5,883,028 A | 3/1999 | Morman et al. |
| 5,914,084 A | 6/1999 | Benson et al. |
| 6,114,263 A | 9/2000 | Benson et al. |

FOREIGN PATENT DOCUMENTS

JP 09 047471 A 2/1997

*Primary Examiner*—Sam Chuan Yao
(74) *Attorney, Agent, or Firm*—Pauley Petersen & Erickson

(57) ABSTRACT

A process for temporarily stabilizing an extensible material while incorporating the material into a garment, or while performing any other converting process on the material. The stabilizing process includes the step of selectively bonding regions of the extensible material to provide a bonded material having restricted extensibility. The bonded material can be put through a converting process, such as winding the bonded material onto a roll, spooling the bonded material, slitting the bonded material, laminating the bonded material, or incorporating the bonded material into a garment. After the bonding material has gone through the converting process, the bonded regions can be removed from the bonded material.

48 Claims, 10 Drawing Sheets

PROCESS FOR TEMPORARILY STABILIZING AN EXTENSIBLE WEB

BACKGROUND OF THE INVENTION

This invention is directed to a process for preventing an extensible web from elongating excessively during handling or converting.

Extensible materials are commonly used in the manufacture of personal care absorbent articles. Converting elastic and extensible materials, namely unwinding the material from a roll or a spool and then performing some operation on it, can be difficult, since some finite tension is required on the web as the web travels through the converting process. Examples of common converting processes include rewinding, spooling, slitting, laminating, or incorporating a web into a complex product such as a diaper.

Converting processes impart tensile forces on a web causing the web to elongate, either permanently or temporarily, thus causing the web's elongational state to change during the process. The effects of the tensile forces can range from minor to extreme. For example, if the material is simply being rewound, then the material's elongational state may be different on the receiving roll versus the feed roll. However, if the material is being converted into a diaper, the elongational state during the process may be so significantly altered as to cause improper placement of diaper components.

There is a need or desire for a way to stabilize an extensible material during handling or converting without eliminating the extensibility of the material.

SUMMARY OF THE INVENTION

This invention is directed to a process for preventing an extensible web from elongating excessively during handling or converting. The process of the invention temporarily stabilizes the extensible web and, once the converting is done, returns full extensibility to the material.

The extensible web used in this invention may be a fibrous material such as, for example, a spunbond web, a meltblown web, a bonded carded web, or a combination thereof. The material may be made of an elastomeric fiber forming polymer.

In carrying out the process of the invention, the web is bonded in specific areas to render the web rigid. The bonding may be, but is not limited to, thermal, ultrasonic, or adhesive bonding, and may stabilize the material against stretching in one direction or in multiple directions. The bonding is suitably oriented in a direction of extensibility of the extensible material, and may also be oriented in other directions non-parallel to the direction of extensibility of the extensible web. Furthermore, the bonding may be either continuous or segmented, and the segmented bond lines may cover varying percentages of the extensible material in the direction of extensibility. The areas that are bonded are suitably areas of the web that will be trimmed or cut away during the converting process.

The converting process may include, but is not limited to, winding the bonded material onto a roll, spooling the bonded material, slitting the bonded material, laminating the bonded material, or incorporating the bonded material into a garment. The extensible material can be incorporated into any suitable personal care garment, such as a diaper, a training pant, a feminine hygiene product, an incontinence product, or a medical garment.

In one embodiment of the invention, the bonded regions may be along the edge regions of the material. By bonding along the edge regions, the bonded regions can easily be removed when stabilization is no longer necessary without disrupting a central region of the material. In this embodiment, the removal of the bonded regions may not require an additional manufacturing step if the bonded regions are located in portions of the material predestined for removal, for example for sizing and/or shaping of a garment made from the extensible material.

In another embodiment of the invention, the bonded regions may be in a central region of the material. The bonded region is then slit to create two pieces of material, each stabilized along one edge. Consequently, the bonded edge regions can easily be removed when stabilization is no longer necessary without disrupting a central region of either of the two pieces of material.

With the foregoing in mind, particular embodiments of the invention provide a process for stabilizing an extensible material during handling or converting without eliminating the extensibility of the material.

The foregoing and other features and advantages of this invention will become further apparent from the following detailed description of the preferred embodiments, read in conjunction with the drawings.

DEFINITIONS

Figure 1:
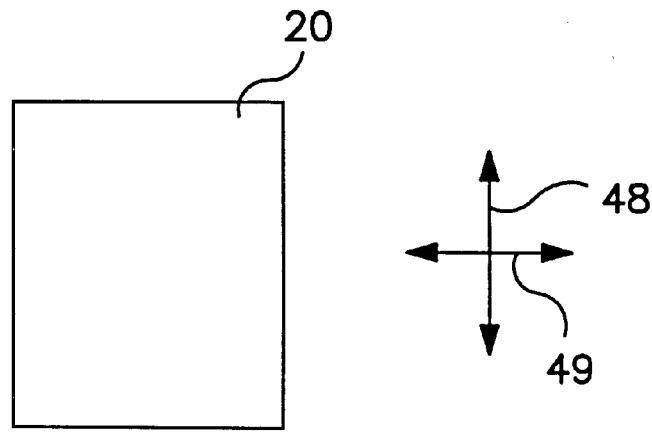
FIG. 1 is a plan view of an exemplary extensible material without bond lines.
Figure 2:
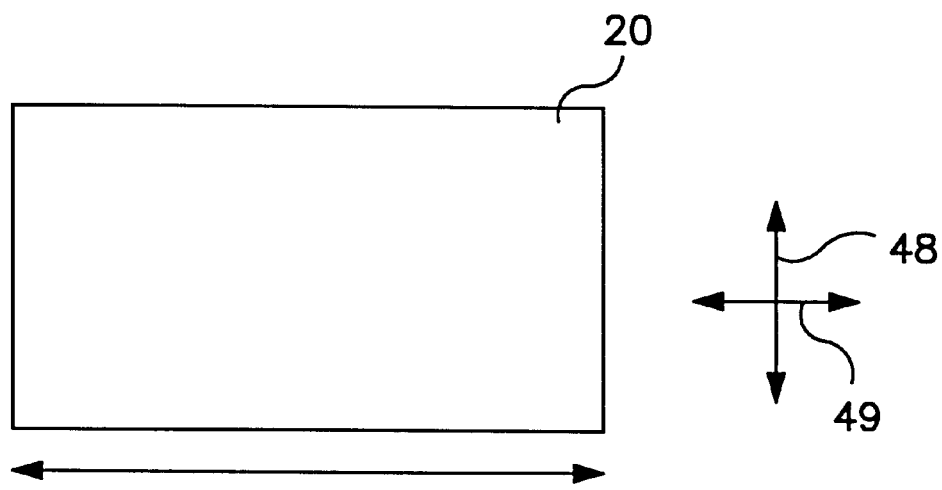
FIG. 2 is a plan view of the exemplary extensible material of FIG. 1 showing the stretchability in one direction, such as the machine direction, when bond lines are not present.

Within the context of this specification, each term or phrase below will include the following meaning or meanings.

"Converting process" refers to any process that requires unwinding the material from a roll or a spool and then performing some operation on the material, such as rewinding the material onto a roll, spooling the material, slitting the material, laminating the material, or incorporating the material into a complex product such as a diaper or other garment.

"Cross direction" refers to the width of a fabric in a direction generally perpendicular to the direction in which it is produced, as opposed to "machine direction" which refers to the length of a fabric in the direction in which it is produced.

"Elastic" and "elastomeric" refer to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to elastic materials and other materials which exhibit the stretching properties of elastic materials without rupture or breakage, including materials that do not recover to the same extent as elastic materials.

"Extensible laminate" refers to a laminate that is extensible in at least one direction by application of a tensioning force in that direction.

"Extensible material" refers to any material which is extensible in at least one dimension by application of a tensioning force in that dimension.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Interfiber bonding" means bonding produced between individual fibers to form a coherent web structure by entanglement, adhesive bonding, or thermal bonding. Fiber entangling is normally a step in a meltblown process but may be generated or increased by processes such as, for example, hydraulic entangling or needle punching. Thermal bonding is normally a step in a spunbonding process. Alternatively and/or additionally, a bonding agent can be utilized to increase the desired bonding and to maintain structural coherency of a fibrous web. For example, powdered bonding agents and chemical solvent bonding may be used.

"Machine direction" refers to the length of a fabric in the direction in which it is produced, as opposed to "cross direction" which refers to the width of a fabric in a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Microfibers" means small diameter fibers having an average diameter not greater than about 50 microns, for example, having a diameter of from about 0.5 microns to about 25 microns, more particularly, microfibers may have an average diameter of from about 1 micron to about 15 microns.

"Necked material" refers to any extensible material which has been narrowed in at least one dimension by application of a tensioning force in another direction.

"Nonwoven" and "nonwoven web" refer to materials and webs of material which are formed without the aid of a textile weaving or knitting process.

"Personal care garment" includes diapers, training pants, swim wear, absorbent underpants, adult incontinence products, feminine hygiene products, medical garments, and the like. The term "medical garment" includes medical (i.e., protective and/or surgical) gowns, caps, gloves, drapes, face masks, blood pressure cuffs, bandages, veterinary products, mortuary products, and the like.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stabilize" refers to the act of maintaining an extensible material in a relatively unextended state, or slightly extended state, in spite of forces acting upon the material.

"Stretchable laminate material" refers to a stretchable material having an elastic sheet joined to an extensible material, such as a creped, gathered, or necked material. The elastic sheet may be joined to the extensible material at intermittent points or may be completely bonded thereto. The joining is accomplished while the elastic sheet and the extensible material are in juxtaposed configuration. The stretchable laminate material is elastic in a direction generally parallel to the direction of extensibility of the extensible material. A stretchable laminate material may include more than two layers. For example, the elastic sheet may have extensible material joined to both of its sides so that a three-layer stretchable laminate material is formed having a structure of extensible material/elastic sheet/extensible material, both extensible materials being extensible in the same direction. Additional elastic sheets and/or extensible material layers may be added. Yet other combinations of elastic sheets and extensible materials may be used.

These terms may be defined with additional language in the remaining portions of the specification.

DETAILED DESCRIPTION OF THE PREFERRED EMBODIMENTS

The present invention is directed to a process for temporarily stabilizing an extensible material to prevent the material from elongating excessively during handling or converting. The process includes the step of selectively bonding a region of the extensible material. The bonded region stabilizes the material during handling, or a converting process, and once stabilization of the material is no longer needed, the bonded region is removed from the rest of the extensible material.

In one embodiment of this invention, a thermal calender bonding process known to those skilled in the art can be used to apply bond lines 22 to the extensible material. In one calendering process, the extensible material 20 can be nipped under light pressure between a patterned steel roller which imparts the bond lines 22 and a smooth anvil roller, with one or both rollers being heated. Other procedures may be utilized to apply bond lines 22 to the material, including other thermal bonding, adhesive bonding and ultrasonic welding. These bond lines 22 may be applied in a direction parallel to the direction of extensibility, or in a direction nonparallel to the direction of extensibility. The extensible material 20 may be extensible in either a cross direction or a machine direction, or in multiple directions including both the cross direction and the machine direction. The width of the extensible material 20 defines the material's cross direction and the length of the extensible material 20 defines the machine direction of the material. For reference, arrows 48 and 49 depicting the orientation of the cross direction and the machine direction, respectively, of the extensible material 20 are illustrated in FIGS. 1–17.

The application of these bond lines 22 to the extensible material 20 can result in an extensible material having regions of higher extensibility with a lower level of interfilament bonding and regions of lower extensibility with a higher level of interfilament bonding corresponding to the bond lines. The stretchability of the extensible material 20 in the cross direction 48, for instance, can be significantly reduced or effectively eliminated by applying bond lines 22 parallel with the cross direction 48. However, the stretchability of the extensible material 20 in the cross direction 48 may not be reduced or may be only nominally reduced by applying bond lines 22 in a direction nonparallel (e.g. perpendicular) to the cross direction 48.

With the application of bond lines 22, a material may be produced that will: (a) have temporarily stabilized extensibility along an entire length of the material in the direction of extensibility; (b) maintain full extensibility in one region of the material and have temporarily stabilized extensibility in a second region of the material; or (c) have regions of varying stabilization of extensibility.

As shown in FIGS. 1–4, the extensible material 20, extensible in a machine direction 49 in this case, can be bonded along edge regions 24 of the material parallel to the machine direction to restrict extensibility of the material in the machine direction. Referring to FIG. 1, when a tensioning force is applied in the machine direction 49 to the extensible material 20 without bond lines 22, the material is highly stretchable and stretches in the machine direction to the dimension shown in FIG. 2.

Figure 3:
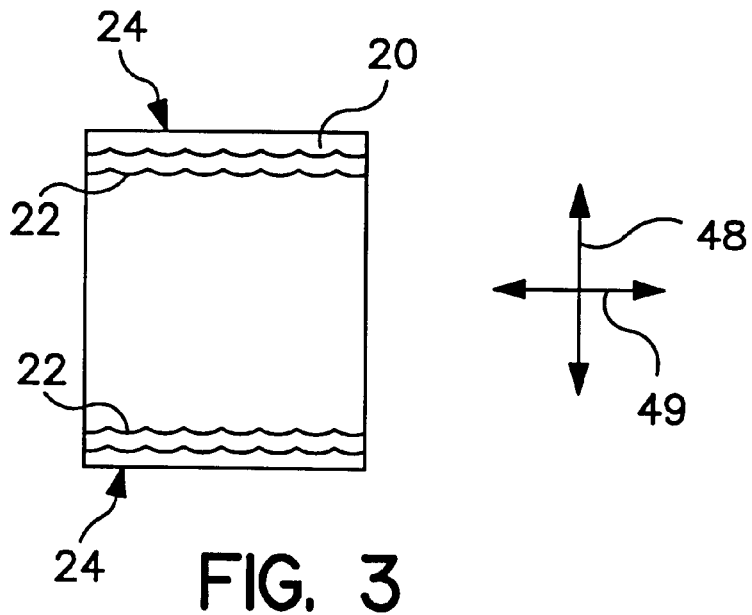
FIG. 3 is a plan view of an exemplary extensible material with bond lines applied along edge regions in one direction, such as the machine direction.
Figure 4:
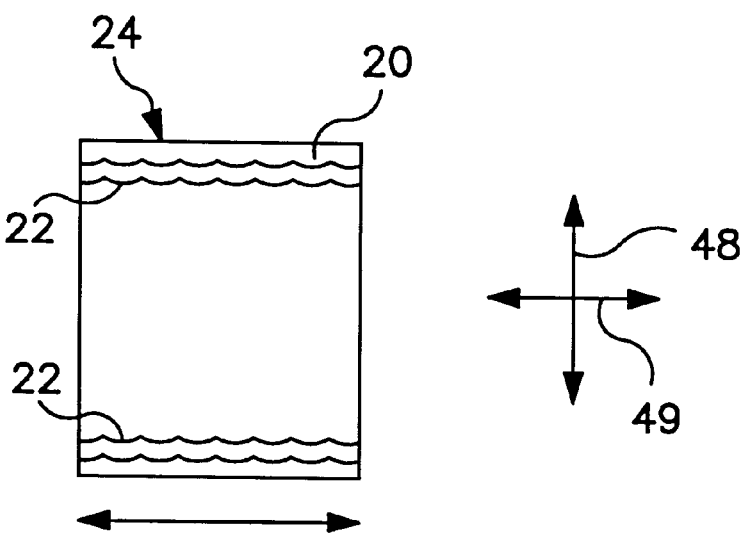
FIG. 4 is a plan view of the exemplary extensible material of FIG. 3 showing the reduction in stretchability in the machine direction when bond lines are applied in the machine direction.

FIG. 3 shows a plan view of a similar extensible material 20 with a series of continuous bond lines 22 applied to edge regions 24 in the direction of extensibility. The application of one or a series of bond lines 22 parallel to the direction of extensibility along at least one edge region 24 significantly decreases or eliminates the stretchability of the material in that direction, as shown in FIG. 4.

The level of extensibility along the bond lines 22 is significantly decreased due to the increased interfilament bonding, attachment and/or densification of the extensible material 20 caused by the thermal calender bonding process. As shown in FIG. 4, when a tensioning force is applied to the material in a direction parallel to bond lines 22 the material will not stretch or only stretch a nominal distance.

Figure 5:
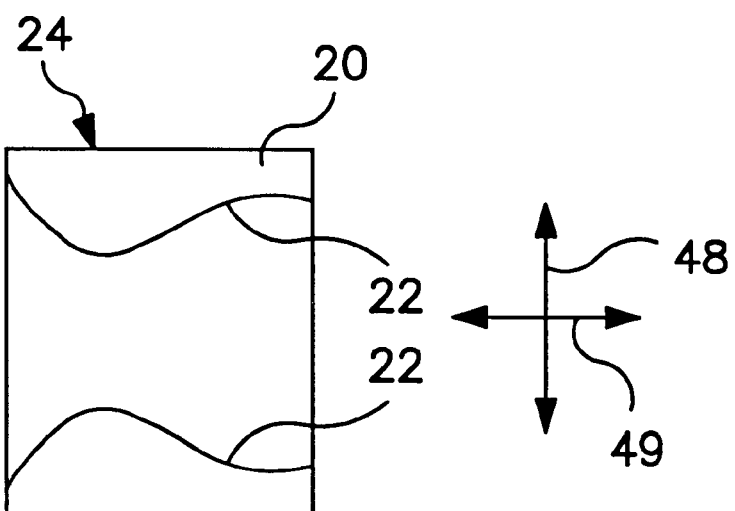
FIG. 5 is a plan view of an exemplary extensible material with bond lines applied nonparallel to edge regions of the material.
Figure 6:
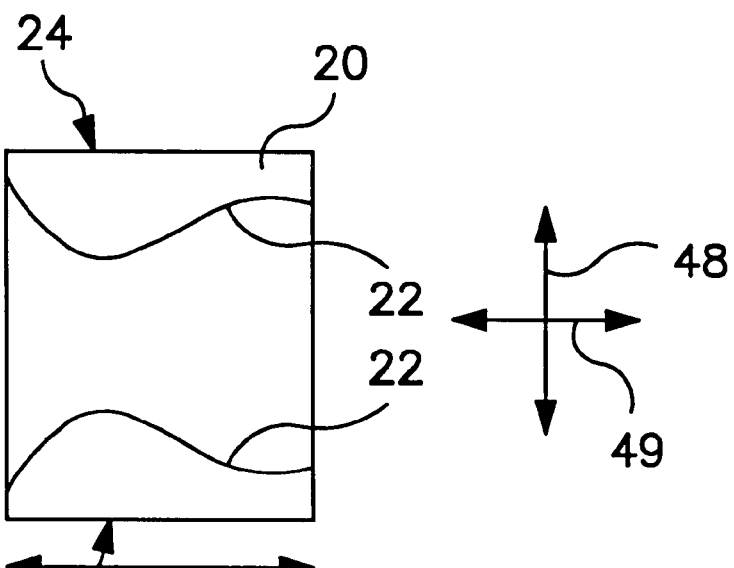
FIG. 6 is a plan view of the exemplary extensible material of FIG. 5 showing the reduction in stretchability in the machine direction when bond lines are applied nonparallel to the edge regions in the machine direction.

FIG. 5 shows a plan view of an extensible material 20 with a series of continuous bond lines 22 nonparallel to a direction of extensibility. When one or a series of bond lines 22 is applied nonparallel to a direction of extensibility of the extensible material 20, the stretchability of the material in the direction of stretch may be stabilized if the bond lines 22 are continuous along the edge regions 24 wherein the edge regions are parallel to the direction of extensibility. As shown in FIG. 6, when a tensioning force is applied to the material 20 in the direction of stretch, the bond lines 22, although nonparallel to the direction of extensibility, stabilize the material because the bond lines 22 are present along the entire edge regions 24 that are parallel to the direction of extensibility. Discontinuity of the bond lines 22 along the edge regions 24 results in decreased stabilization of the material.

Figure 7:
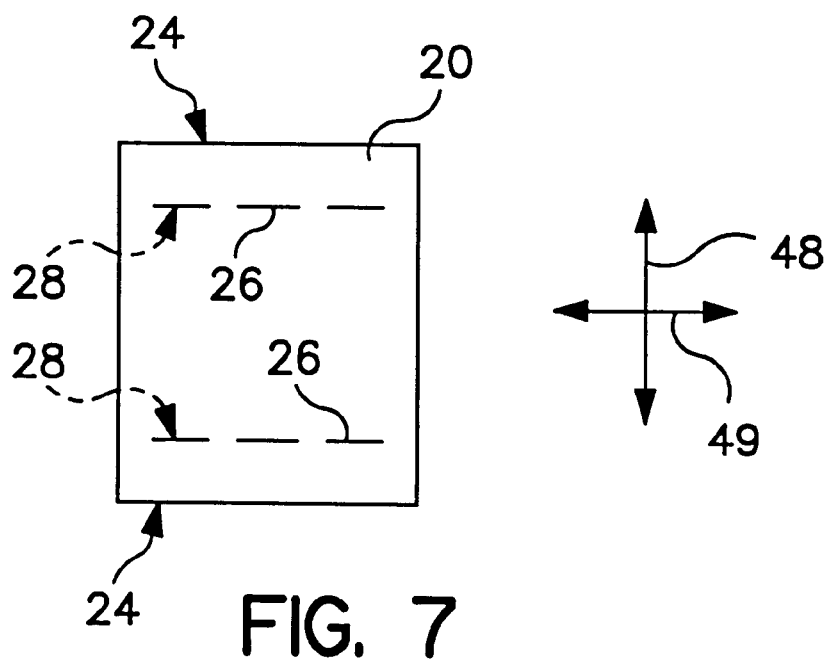
FIG. 7 is a plan view of an exemplary extensible material with variable bond lines applied to edge regions of the material in the machine direction.

The reduction in stretchability which results from applying bond lines 22 to the extensible material 20 can easily be controlled and varied. The continuous bond lines 22 as shown in FIGS. 3–6 can be separated into a plurality of noncontinuous bond line segments 26 as shown in FIG. 7 to form dashed, noncontinuous bond lines 28. The length of the individual bond line segments 26, the number of bond line segments 26 comprising a noncontinuous bond line 28, and the distance between them affect the stretchability of the material. In one embodiment of this invention, the bond line segments 26 that make up the noncontinuous bond line 28 are of about equal length and spacing. However, in other embodiments of this invention, bond line segments 26 may be of nonuniform lengths and/or spacing to effect nonuniform stretching. Further, in yet another embodiment of this invention, successive noncontinuous bond lines 28 may be composed of bond line segments 26 of about equal lengths and spacing, or each successive bond line 28 may include bond line segments 26 of varying uniform or nonuniform lengths and/or spacing.

Figure 8:
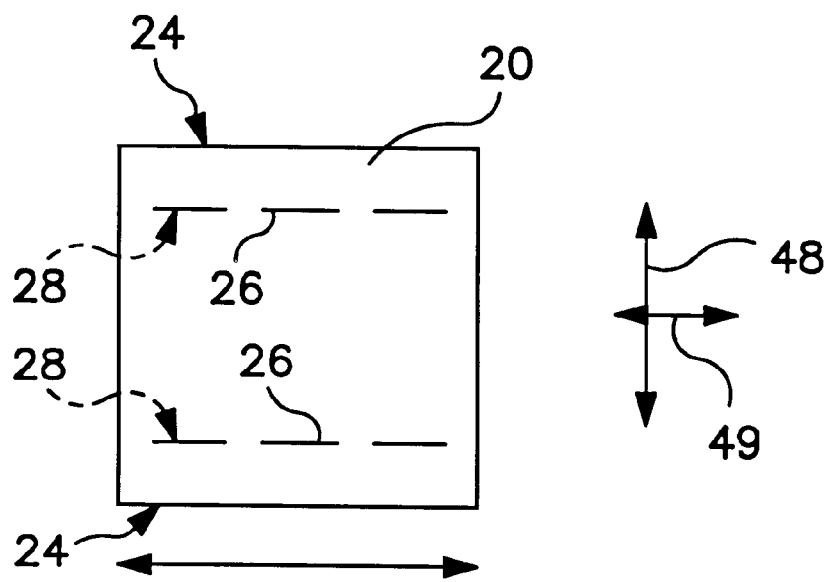
FIG. 8 is a plan view of the exemplary extensible material of FIG. 7 showing the reduction in stretchability in the machine direction when variable bond lines are applied to edge regions of the material in the machine direction. Most of the stretching occurs in the spaces between the bond line segments.

FIG. 8 shows a plan view of the extensible material 20 of FIG. 7 showing the effects of noncontinuous bond lines 28 on the stretchability of a material in a direction parallel with the bond lines 28.

The Reduction in Stretchability ($R_S$) of the extensible material when bond lines 28 are applied can be represented as follows:

$$R_S = f(W_b, S_i);$$

where $W_b$ represents the fraction of material width in the direction of extensibility occupied by a bond line 28 and $S_i$ represents the initial stretchability of the material 20 in the direction of extensibility. This means that $R_s$ is a function of $W_b$ and $S_i$. If the extensibility is zero at the precise location of a bond line 28, then $R_s$ is at its maximum value of 1.0.

FIGS. 7 and 8 show a plan view of an extensible material 20 and the reduction in stretchability exhibited when a tensioning force is applied to the material in the machine direction 49, or direction of extensibility. The illustrated extensible material 20 has an initial stretchability (without bond lines) of 200% in the direction of stretch, e.g. the machine direction. Assuming $R_s$ is directly proportional to the function of material bonded, as in an ideal situation, a series of noncontinuous bond lines 28 occupying six-tenths of the material length in the machine direction will reduce the extensibility of the material by about six-tenths, from 200% to 80%, when a tensioning force is applied, i.e. $R_S = 0.60 * 200\% = 120\%$.

In another embodiment of this invention, a biaxially stretchable elastic nonwoven web, or a necked stretched bonded nonwoven laminate (NSBL) material including a stretched elastic sheet thermally bonded to a necked nonwoven (e.g. spunbond) web is produced by a procedure discussed below. The elastic nonwoven web, or the necked stretched bonded laminate material, is capable of stretching in all directions. Bond lines 22 or 28 can be applied by the thermal calender bonding process discussed above, or by another process, to produce a material having regions wherein bond lines 22, 28 are applied to edge regions 24 parallel to the cross direction 48 and having regions wherein bond lines 22,28 are applied to edge regions 24 nonparallel to the cross direction, preferably perpendicular to the cross direction, i.e. in the machine direction. The extensibility in either the cross direction 48 or the machine direction 49 of a region of the material 20 is reduced or effectively eliminated by applying bond lines 22, 28 to the edge regions 24. The bond lines 22, 28 may be continuous or noncontinuous.

Figure 9:
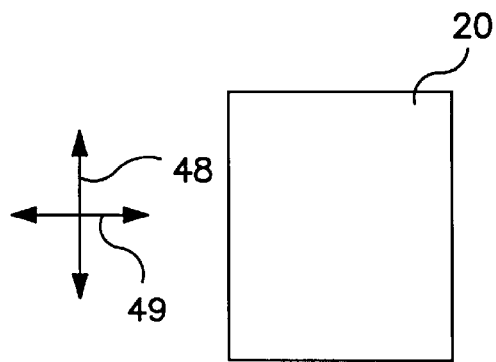
FIG. 9 is a plan view of an exemplary extensible material, extensible in multiple directions, with no bond lines present.
Figure 10:
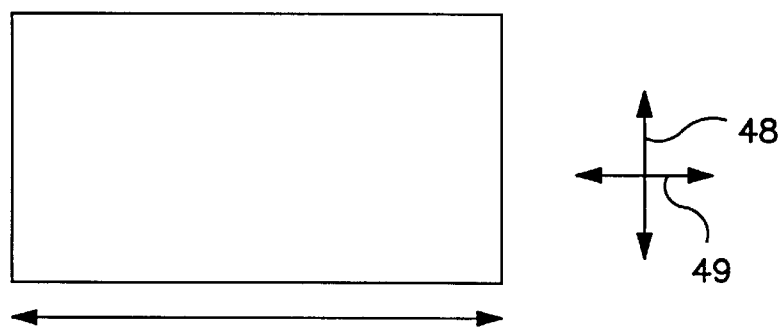
FIG. 10 is a plan view of the exemplary extensible material of FIG. 9, showing the stretchability of the material in the machine direction when bond lines are not present.
Figure 11:
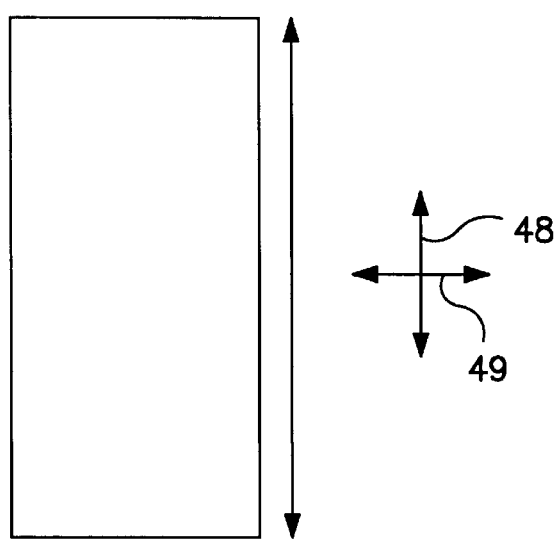
FIG. 11 is a plan view of the exemplary extensible material of FIG. 9, showing the stretchability of the material in the cross direction when bond lines are not present.

FIG. 9 illustrates an elastic spunbond nonwoven web or elastic NSBL material 20 with no bond lines. This material can be stretched in the machine direction 49 (See FIG. 10) and the cross direction 48 (See FIG. 11).

Figure 12:
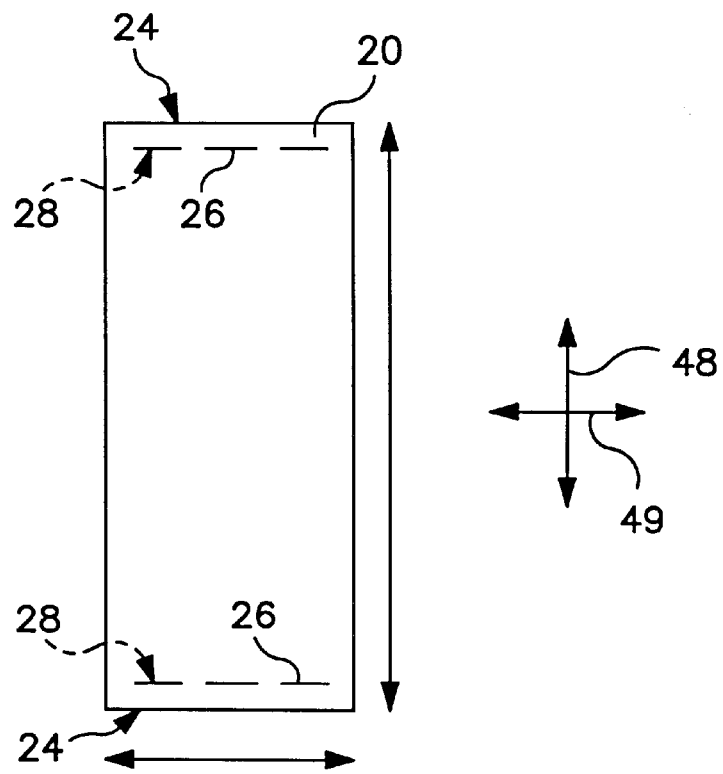
FIG. 12 is a plan view of the exemplary extensible material of FIG. 9, showing the effects on stretchability of the material in the cross direction and in the machine direction when bond lines are applied to the material in the machine direction along two edge regions of the material.
Figure 13:
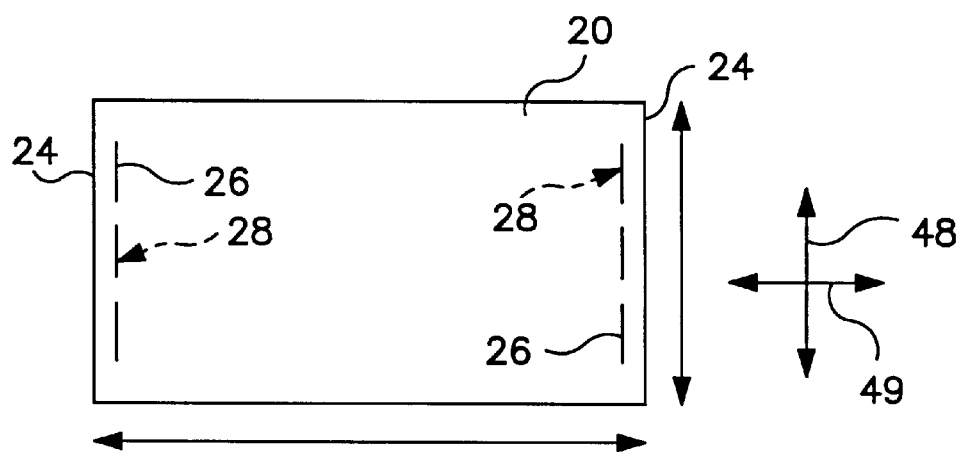
FIG. 13 is a plan view of the exemplary extensible material of FIG. 9, showing the effects on stretchability of the material in the cross direction and in the machine direction when bond lines are applied to the material in the cross direction along two edge regions of the material.
Figure 14:
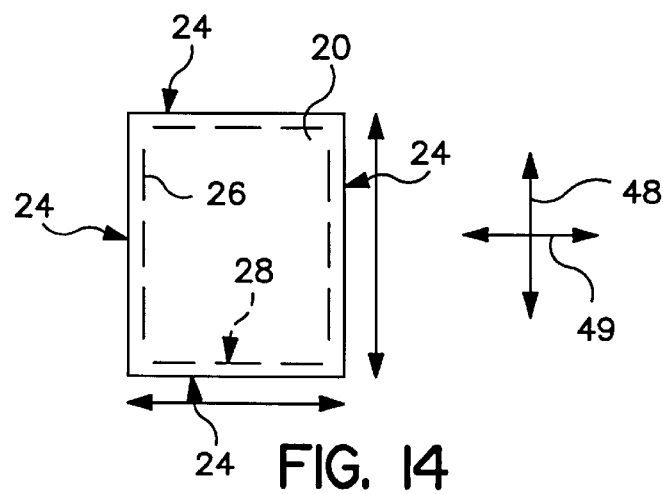
FIG. 14 is a plan view of the exemplary extensible material of FIG. 9, showing the effects on stretchability of the material in the cross direction and in the machine direction when bond lines are applied to the material in the cross direction along two edge regions of the material and in the machine direction along two other edge regions of the material.

As shown in FIGS. 12–14, when bond lines 22 and/or 28 are applied to edge regions 24 of the extensible material 20, the material exhibits zoned stretching. As shown in FIG. 12, when a tensioning force is applied to the material 20 in both the cross direction 48 and the machine direction 49, the bond lines 28 that are parallel to the machine direction stabilizes the material in the machine direction and therefore the material 20 stretches in the machine direction to a lesser extent than in the cross direction when no bond lines 22 and/or 28 are parallel to the cross direction. Conversely, as shown in FIG. 13, when a tensioning force is applied to the material 20 in both the cross direction 48 and the machine direction 49, the bond lines 28 that are parallel to the cross direction stabilizes the material in the cross direction and therefore the material 20 stretches in the cross direction to a lesser extent than in the machine direction when no bond lines 22 and/or 28 are parallel to the machine direction. Furthermore, as shown in FIG. 14, when a tensioning force is applied to the material 20 in both the cross direction 48 and the machine direction 49, bond lines 28 that are parallel to the cross direction stabilize the material in the cross direction and bond lines 28 that are parallel to the machine direction stabilize the material in the machine direction, thereby stabilizing the material in both the cross direction and the machine direction.

Figure 15:
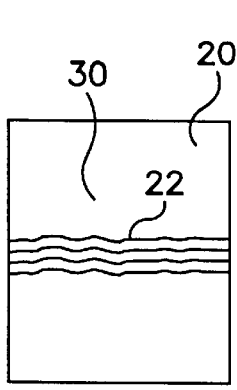
FIG. 15 is a plan view of an exemplary extensible material with bond lines applied to a central region of the material in one direction, such as the machine direction.
Figure 16:
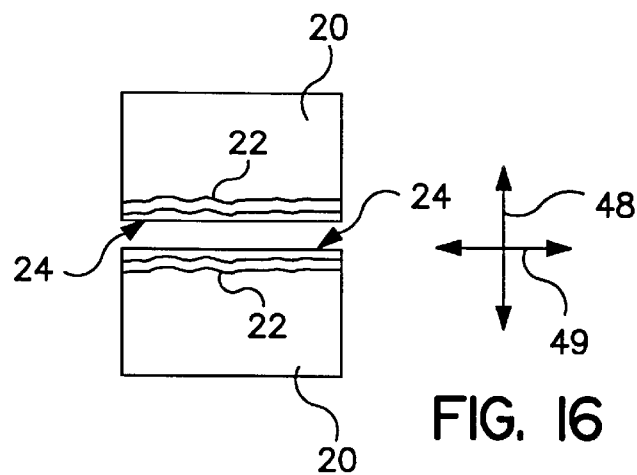
FIG. 16 is a plan view of the exemplary extensible material of FIG. 15 showing the bonded central region slit in half forming two pieces of extensible material each having a bonded edge region.

In another embodiment of the invention, the bond lines 22 are not located along the edge regions 24 of the material 20 but instead are located in a central region 30 of the material, as shown in FIG. 15. In this embodiment, once the bonded region 22 is formed, the bonded region is slit to form at least two separate pieces of extensible material 20, each of the pieces of extensible material having a bonded edge region 24.

The bond lines 22, 28 which are used to effect the controlled extensibility are distinguishable from the interfilament bond patterns already existing in a nonwoven web, and from the inter-layer bonding in a laminate. Typically, the bond lines 22, 28 used to effect controlled extensibility are relatively long and narrow, and substantially straight (i.e. directionally oriented). The individual bond line segments 26 (if the lines are discontinuous) typically have a length of at least 0.1 inch, preferably at least about 0.2 inch, more preferably at least about 0.3 inch. If an individual bond line 28 is segmented, the segments are substantially aligned. The overall bond line length (i.e. the sum total of aligned segment length, or total line length, if not segmented) is typically at least about 0.5 inch, suitably at least about 1.0 inch, or at least about 1.5 inches. The bond line segments 26 have greater lengths than widths. Typically, a bond line segment 26 has a length/width ratio (L/D) of at least 2.0, suitably at least 3.0, or at least 4.0. Typically, the L/D of the overall bond lines (i.e. based on the sum of the segment lengths, or the total bond length if continuous) is at least about 10, preferably at least about 15, more preferably at least about 20. The spacing between adjacent (e.g. parallel) bond lines 22, 28 can also be varied and is generally at least about 0.1 inch, suitably at least about 0.2 inch, or at least about 0.3 inch.

The spunbond bond sites (imparted during manufacture of the web) are in place before necking the spunbond web, and allow it to neck. Without these bond sites, the material would pull apart. These bond sites are uniformly spaced, and do not selectively inhibit stretching. Further bonding filaments, in accordance with the invention when the spunbond is necked, inhibits the stretching in the cross direction.

Temporary stabilization of the extensible material 20 is helpful while handling and converting the material, thereby preventing or minimizing deformation of the material during handling and/or converting. The converting process involved in the process of the invention may include winding the bonded material onto a roll, spooling the bonded material, slitting the bonded material, laminating the bonded material, or incorporating the bonded material into a garment. The process of stabilizing the extensible material may be particularly suitable when incorporating the material into a personal care garment, such as a diaper, a training pant, a feminine hygiene product, an incontinence product, or a medical garment. Once the material has been converted, or during a converting process, or at a point when stabilization of the extensible material is no longer needed, the bonded areas can be cut away. Once the bonded areas are cut away, the material can regain its extensibility.

Figure 17:
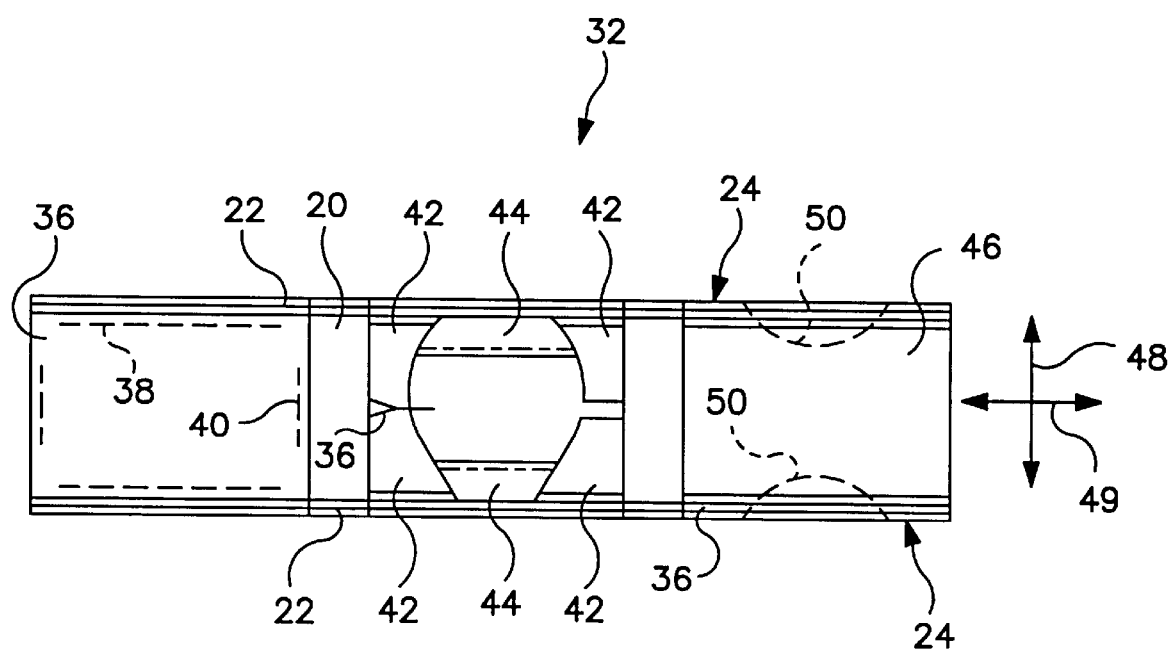
FIG. 17 is a plan view of a machine direction assembly for assembling diapers.

As an example of a converting process, the extensible material can be used to make an outer cover 36 of a diaper. A machine direction assembly 32 in a diaper-assembly process is shown in FIG. 17. An elastic laminate without bonded edge regions experiences a variety of machine-directional tensile stresses as it travels through the diaper assembly process. The tensile stresses cause the unbonded laminate to elongate and relax uncontrollably during the process, resulting in misplacement of other elements of the diaper onto the outer cover. By thermally bonding the outer cover material 20 beforehand, such that the bonded regions 22 are only present along the edge regions 24 of the material, the ability of the web to elongate in the machine direction 49 during converting is significantly diminished. While the material is in the stabilized state, a number of various components can be attached to the outer cover 36, including leg elastics 38, waist elastics 40, side panels 42, containment flaps 44, or other layers such as an absorbent assembly, surge layer or body side liner 46. Toward the end of the converting process, leg openings 50 can be cut in the outer cover material, thereby cutting away a large portion of the thermally bonded area. The outer cover 36 is then free to stretch in the final product.

Figure 18:
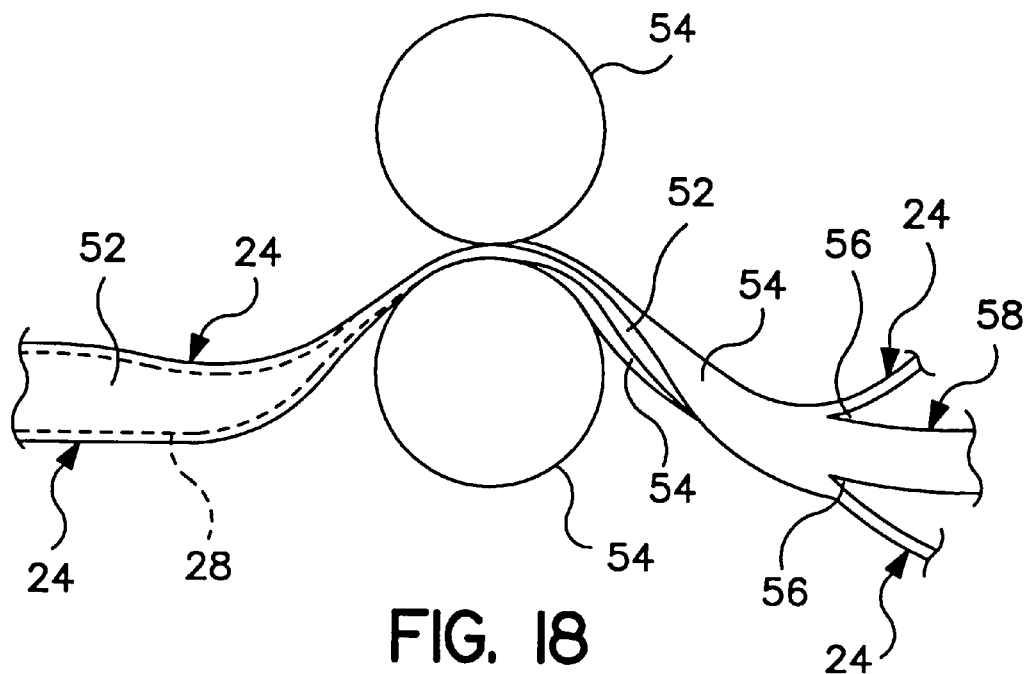
FIG. 18 is a plan view of a lamination process involving an exemplary extensible material with bonded edge regions.

As another example of a converting process, creped spunbond 52, which is extensible in the machine direction 49, may be thermally bonded on the edge regions 24 parallel to the machine direction to prevent stretching when the material is unwound into a lamination process, shown in FIG. 18. During the lamination process, the creped spunbond 52 can be laminated between two additional nonwoven webs 54. At the end of the lamination process, the material can be put through a slitting device 56 that trims away the bonded edge regions 24, thereby freeing the laminate 58 to be machine direction extensible.

Figure 19:
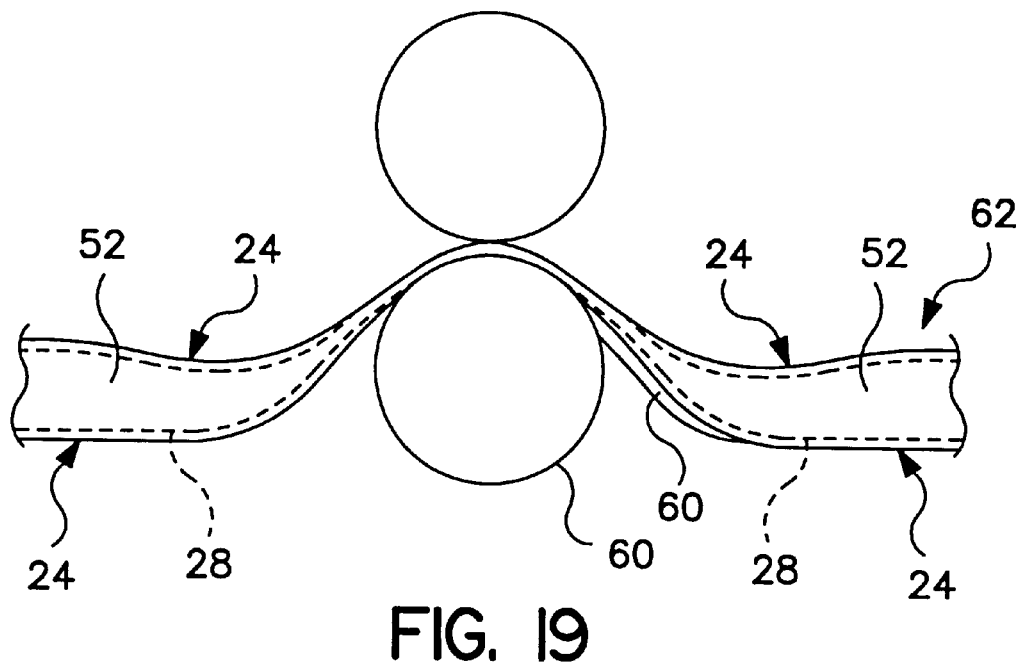
FIG. 19 is a plan view of another lamination process involving an exemplary extensible material with bonded edge regions.

Yet another example of a converting process, illustrated in FIG. 19, is a creped spunbond 52, stabilized as described above, laminated to an elastic film 60, thereby creating a stabilized laminate 62. In this case, the stabilized creped spunbond 52 is acting as the stabilizing element for the entire laminate 62. The laminate 62 may then be converted and the stabilizing areas cut away as described above.

Figure 20:
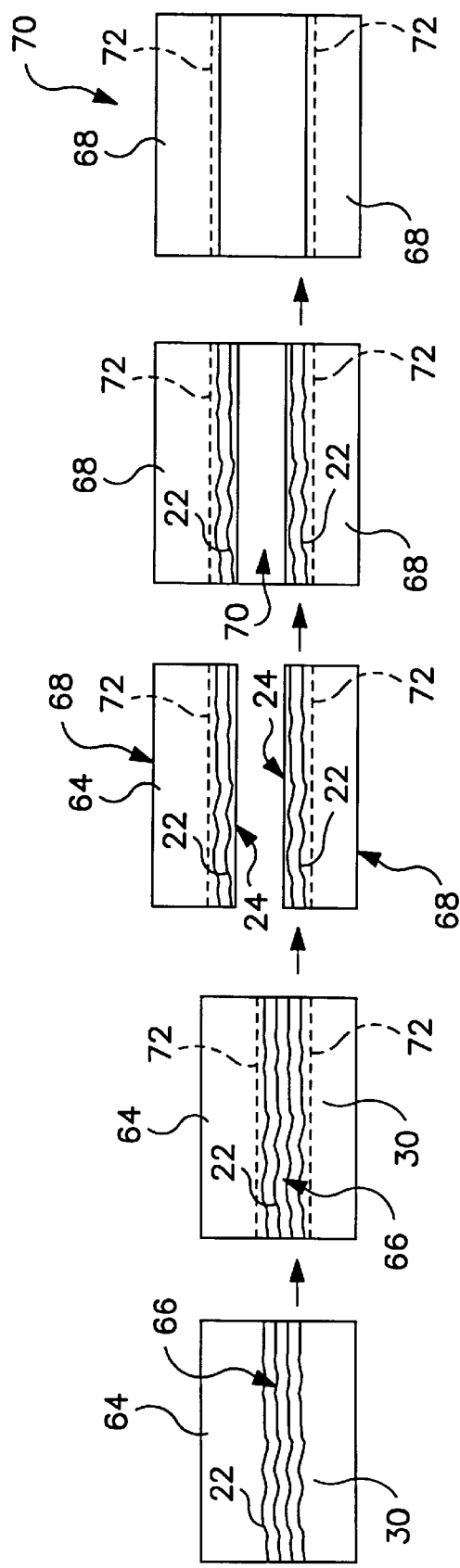
FIG. 20 is a plan view of a converting process carried out on an exemplary extensible material with bond lines applied to a central region of the material.

A further example of a converting process, illustrated in FIG. 20, includes an elastic laminate 64 bonded in a central region 30 to stabilize the material. The material 64 can be used to form leg cuffs 68, or containment flaps, for attachment to a diaper chassis 70. Elastic strands 72 can be attached to the material 64 parallel to the bonded region 66. The stabilized material 64 can be slit in half through the bonded area 66 either prior to or subsequent to attaching the leg elastics 72, resulting in two pieces of extensible material that are each stabilized along an edge region 24. The stabilized leg cuffs 68 can be attached to the diaper chassis 70 in the stabilized state and can subsequently have the bonded regions trimmed away to return extensibility to the leg cuffs.

In one embodiment of this invention, the extensible material 20 can be an elastomeric nonwoven web. The elastomeric nonwoven web may be, for example, a spunbond web, a meltblown web, a bonded carded web, or a combination thereof. If the material is a web of meltblown fibers, it may include meltblown microfibers. The material may be made of elastomeric fiber forming polymers. The extensible material suitably can be stretched between about 50% and about 200%, or between about 70% and about 170%, or between about 100% and about 150%.

More particularly, the extensible material may include thermoplastic elastomeric fibers made of diblock, triblock, or multi-block elastomeric copolymers such as olefinic copolymers, including styrene-isoprene-styrene, styrene-butadienestyrene, styrene-ethylene/butylene-styrene, or styrene-ethylene/propylene-styrene, which may be obtained from the Shell Chemical Company, under the trade designation KRATON® elastomeric resin; polyurethanes, including those available from E.I. Du Pont de Nemours Co., under the trade name LYCRA® polyurethane; polyamides, including polyether block amides available from Ato Chemical Company, under the trade name PEBAX® polyether block amide; polyesters, such as those available from E.I. Du Pont de Nemours Co., under the trade name HYTREL® polyetherester; and single-site or metallocene-catalyzed polyolefins having density less than about 0.89 grams/cc, available from Dow Chemical Co. under the trade name AFFINITY®.

Elastomeric meltblown webs may be produced using conventional meltblowing processes and apparatus as known in the art, for example as disclosed in U.S. Pat. No. 3,849,241 to Butin et al. In meltblowing, a thermoplastic resin, here an elastomeric resin, is fed into an extruder where it is melted and heated to an appropriate temperature required for fiber formation. The extruder feeds molten resin to a special meltblowing die. The resin emerges from the die orifices as molten threads into a high velocity stream of gas, usually air. The air attenuates the polymer into a blast of fine fibers which are collected on a moving screen placed in front of the blast. As the fibers land on the screen, they entangle to form a cohesive web.

Elastomeric spunbond webs employed in this invention may be formed by techniques known in the art, for example techniques described in U.S. Pat. No. 4,340,563 to Appel et al.; U.S. Pat. No. 3,692,618 to Dorschner et al.; and U.S. Pat. No. 3,802,817 to Matsuki et al. Examples of polymers which may be suitably used to form spunbond webs include the elastomeric polymers listed above.

The extensible material may be a single-layer material as described above. For example, the material may be a spunbond web having a basis weight of about 0.2–10 ounces per square yard ("osy"), or a meltblown web having a basis weight of about 0.2–8 osy. Alternatively, the extensible material may be a multilayer material having, for example, at least one layer of spunbond web bonded to at least one layer of meltblown web, bonded carded web or other suitable material. For example, a material may include a multilayer material having a first layer of spunbond polypropylene having a basis weight from about 0.2 to about 8 osy, a layer of meltblown polypropylene having a basis weight from about 0.2 to about 4 osy, and a second layer of spunbond polypropylene having a basis weight of about 0.2 to about 8 osy.

The extensible material may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324, the disclosure of which is hereby incorporated by reference.

If the extensible material is a nonwoven web of fibers, the fibers may be joined by interfiber bonding to form a coherent web structure. Interfiber bonding may be produced by thermal bonding in a spunbonding process, or entanglement between individual meltblown fibers. The fiber entangling is inherent in the meltblown process but may be generated or increased by processes such as, for example, hydraulic entangling or needlepunching. Alternatively and/or additionally a bonding agent may be used to increase the desired bonding.

In another embodiment of this invention, the extensible material can be a stretchable laminate material including an elastic film and a neckable web. One process for forming a stretchable necked-bonded laminate material is disclosed in U.S. Pat. No. 5,883,028 issued to Morman et al., the disclosure of which is hereby incorporated by reference.

The elastic sheet may be a single layer or multilayer material, including one or more individual coherent webs, films and/or foams. Additionally, the elastic sheet may be a single layer or multilayer material in which one or more of the layers contain a mixture of elastic and nonelastic fibers or particulates. The elastic sheet may be formed from one or more of the elastic polymers listed above.

Elastic sheets can be used having basis weights less than 0.5 osy (ounces per square yard), for example, from about 0.25 to about 0.4 osy. Such extremely low basis weight sheets are advantageous because of higher breathability and economic reasons, and are particularly useful in disposable products. Additionally, elastic sheets having higher basis weights such as, for example, from about 0.5 to about 10 osy, or about 11 to about 40 osy, may also be used.

Necked materials may be joined to the elastic sheet by any suitable means such as, for example, thermal or adhesive bonding or ultrasonic welding which softens at least portions of at least one of the materials, usually the elastic sheet because the elastomeric materials used for forming the elastic sheet have a lower softening point than the components of the necked material. The necked material and the elastic sheet may be completely bonded together and still provide a stretchable laminate material with good stretch properties. Joining may be produced by applying heat and/or pressure to the overlaid elastic sheet and the necked material by heating these portions (or the overlaid layer) to at least the softening temperature of the material with the lowest softening temperature to form a reasonably strong and permanent bond between the re-solidified softened portions of the elastic sheet and the necked material. Conditions should not be so severe as to perforate the film. Suitable bonding conditions are described in the above-mentioned U.S. Pat. No. 5,883,028 to Morman et al.

In another neck-bonded laminate, the elastic sheet (i.e. film, foam or web) may be stretched in a direction other than parallel (e.g., perpendicular) to the direction of necking of the nonwoven web, and laminated to the neckable nonwoven web in a plurality of spaced apart locations while the sheet is in the stretched condition and while the web is necked. After lamination, the elastic sheet is relaxed, causing puckering or gathering of the web between the bonded regions. The resulting composite laminate is initially stretchable in at least two nonparallel directions. The stretchability of the composite in the directions parallel to the direction of necking is facilitated by the necking of the web. The stretchability of composite in the direction nonparallel (e.g., perpendicular) to the direction of necking is facilitated by the gathering of the web in that direction. Processes for making a multidirectional stretchable laminate from an elastic sheet and necked nonwoven web are described in U.S. Pat. Nos. 5,116,662 and 5,114,781, both issued to Morman, the disclosures of which are incorporated herein by reference.

Other layer combinations are also possible for controlled stretch laminates for use in this invention. For these aspects of the invention, the laminate material should include at least one elastic sheet and at least one necked or un-necked nonwoven (preferably spunbond) layer. In one embodiment, a reversibly necked nonwoven web may be laminated to an elastic film, as described in U.S. Pat. No. 5,114,781 issued to Morman.

In another embodiment of this invention, the extensible material can be a stretch-bonded laminate material comprising an elastic nonwoven web or an elastic film and a gatherable web or webs. One process for forming a stretch-bonded laminate is disclosed in U.S. Pat. No. 4,720,415, issued to Vander Wielen et al., hereby incorporated by reference. Stretch-bonded laminates are particularly useful in this invention.

Using a gatherable, unnecked, nonwoven web for the above-described process would produce a laminate that stretches only in the direction that the elastic sheet was stretched prior to bonding. Such a process, and the resulting stretch-bonded laminates, are described in U.S. Pat. No. 4,720,415, issued to Vander Wielen et al. Stretch-bonded laminates that have elastic stretch in the machine direction are particularly useful in this invention.

In accordance with this invention, an extensible material can be temporarily stabilized to facilitate handling of the material during a converting process. Once stabilization of the material is no longer necessary, the extensibility of the material can be returned to the material.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A process for stabilizing an extensible material during a converting process, comprising the steps of:

providing an extensible material having a level of extensibility;

selectively bonding edge regions of the extensible material to provide a bonded material having restricted extensibility;

performing an operation on the bonded material, selected from the group consisting of winding the bonded material onto a roll, spooling the bonded material, slitting the bonded material, laminating the bonded material, and incorporating the bonded material into a garment; and removing the bonded edge regions from the bonded material.

2. The process of claim 1, wherein the extensible material comprises a material selected from the group consisting of spunbond webs, meltblown webs, bonded carded webs, and combinations thereof.

3. The process of claim 1, wherein the extensible material comprises an elastic polymer selected from the group consisting of diblock, triblock, or multi-block elastomeric copolymers such as olefinic copolymers, including styrene-isoprene-styrene, styrene-butadiene-styrene, styrene-ethylene/butylene-styrene, or styrene-ethylene/propylene-styrene, polyurethanes, polyamides, including polyether block amides, polyesters, and single-site or metallocene-catalyzed polyolefins having a density less than about 0.89 grams/cc.

4. The process of claim 1, wherein the extensible material comprises a stretch-bonded laminate.

5. The process of claim 1, wherein the extensible material comprises a necked-bonded laminate.

6. The process of claim 1, wherein the extensible material can be stretched between about 50% and about 200%.

7. The process of claim 1, wherein the extensible material can be stretched between about 70% and about 170%.

8. The process of claim 1, wherein the extensible material can be stretched between about 100% and about 150%.

9. The process of claim 1, wherein the bonded edge regions are oriented in a direction of extensibility of the extensible material.

10. The process of claim 1, wherein the bonded edge regions comprise continuous bonding lines oriented in a direction of extensibility.

11. The process of claim 1, wherein the bonded edge regions comprise segmented bonding lines oriented in a direction of extensibility.

12. The process of claim 1, wherein the bonded edge regions comprise segmented bond lines covering varying percentages of the extensible material in a direction of extensibility.

13. The process of claim 1, wherein the bonded edge regions comprise a first bonding line, and a second bonding line non-parallel to the first bonding line.

14. The process of claim 1, wherein the bonding step comprises thermal bonding.

15. The process of claim 1, wherein the bonding comprises adhesive bonding.

16. The process of claim 1, wherein the bonding comprises ultrasonic bonding.

17. A process for making a garment having an extensible layer, comprising the steps of:

providing an extensible material having a level of extensibility;

selectively bonding edge regions of the extensible material to provide a bonded material having restricted extensibility;

converting the bonded material into a garment; and removing the bonded edge regions from the bonded material.

18. The process of claim 17, wherein the extensible material comprises a material selected from the group consisting of spunbond webs, meltblown webs, bonded carded webs, and combinations thereof.

19. The process of claim 17, wherein the extensible material comprises an elastic polymer selected from the group consisting of diblock, triblock, or multi-block elastomeric copolymers such as olefinic copolymers, including styrene-isoprene-styrene, styrene-butadiene-styrene, styrene-ethylene/butylene-styrene, or styrene-ethylene/propylene-styrene, polyurethanes, polyamides, including polyether block amides, polyesters, and single-site or metallocene-catalyzed polyolefins having a density less than about 0.89 grams/cc.

20. The process of claim 17, wherein the extensible material comprises a stretch-bonded laminate.

21. The process of claim 17, wherein the extensible material comprises a necked-bonded laminate.

22. The process of claim 17, wherein the bonded edge regions are oriented in a direction of extensibility of the extensible material.

23. The process of claim 17, wherein the bonded edge regions comprise continuous bonding lines oriented in a direction of extensibility.

24. The process of claim 17, wherein the bonded edge regions comprise segmented bonding lines oriented in a direction of extensibility.

25. The process of claim 17, wherein the bonded edge regions comprise segmented bond lines covering varying percentages of the extensible material in a direction of extensibility.

26. The process of claim 17, wherein the bonded edge regions comprise a first bonding line, and a second bonding line non-parallel to the first bonding line.

27. The process of claim 17, wherein the bonding step comprises thermal bonding.

28. The process of claim 17, wherein the bonding comprises adhesive bonding.

29. The process of claim 17, wherein the bonding comprises ultrasonic bonding.

30. The process of claim 17, wherein the garment comprises a personal care garment.

31. The process of claim 17, wherein the garment comprises a diaper.

32. The process of claim 17, wherein the garment comprises a training pant.

33. The process of claim 17, wherein the garment comprises a feminine hygiene product.

34. The process of claim 17, wherein the garment comprises an incontinence product.

35. The process of claim 17, wherein the garment comprises a medical garment.

36. A process for making a garment having an extensible layer, comprising the steps of:

providing an extensible material having a level of extensibility;

selectively bonding a region of the extensible material to provide a bonded material having restricted extensibility;

slitting the bonded region to form at least two pieces of extensible material, each of the pieces of extensible material having a bonded edge;

converting the at least two pieces of extensible material into a garment; and removing the bonded edge regions from the at least two pieces of extensible material.

37. The process of claim 36, wherein the extensible material comprises a material selected from the group consisting of spunbond webs, meltblown webs, bonded carded webs, and combinations thereof.

38. The process of claim 36, wherein the extensible material comprises an elastic polymer selected from the group consisting of diblock, triblock, or multi-block elastomeric copolymers such as olefinic copolymers, including styrene-isoprene-styrene, styrene-butadiene-styrene, styrene-ethylene/butylene-styrene, or styrene-ethylene/propylene-styrene, polyurethanes, polyamides, including polyether block amides, polyesters, and single-site or metallocene-catalyzed polyolefins having a density less than about 0.89 grams/cc.

39. The process of claim 36, wherein the extensible material comprises a stretch-bonded laminate.

40. The process of claim 36, wherein the extensible material comprises a necked-bonded laminate.

41. The process of claim 36, wherein the bonded edge regions are oriented in a direction of extensibility of the extensible material.

42. The process of claim 36, wherein the bonded edge regions comprise continuous bonding lines oriented in a direction of extensibility.

43. The process of claim 36, wherein the bonded edge regions comprise segmented bonding lines oriented in a direction of extensibility.

44. The process of claim 36, wherein the bonded edge regions comprise segmented bond lines covering varying percentages of the extensible material in a direction of extensibility.

45. The process of claim 36, wherein the bonded edge regions comprise a first bonding line, and a second bonding line non-parallel to the first bonding line.

46. The process of claim 36, wherein the bonding step comprises thermal bonding.

47. The process of claim 36, wherein the bonding comprises adhesive bonding.

48. The process of claim 36, wherein the bonding comprises ultrasonic bonding.

* * * * *